(12) United States Patent
Grass et al.

(10) Patent No.: US 9,493,632 B2
(45) Date of Patent: *Nov. 15, 2016

(54) DIANHYDROHEXITOL DIESTER MIXTURE GC

(71) Applicant: Evonik Degussa GmbH, Essen (DE)

(72) Inventors: Michael Grass, Haltern am See (DE); Andreas Gevers, Bottrop (DE); Benjamin Woldt, Marl (DE); Michael Woelk-Faehrmann, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/367,636

(22) PCT Filed: Dec. 19, 2012

(86) PCT No.: PCT/EP2012/076064
§ 371 (c)(1),
(2) Date: Jun. 20, 2014

(87) PCT Pub. No.: WO2013/092649
PCT Pub. Date: Jun. 27, 2013

(65) Prior Publication Data
US 2015/0152245 A1    Jun. 4, 2015

(30) Foreign Application Priority Data

Dec. 21, 2011 (DE) .......... 10 2011 089 495

(51) Int. Cl.
*C08K 5/1535* (2006.01)
*C07D 493/04* (2006.01)

(52) U.S. Cl.
CPC .......... *C08K 5/1535* (2013.01); *C07D 493/04* (2013.01)

(58) Field of Classification Search
CPC ............ C07D 493/04; C08K 5/1535
USPC ............................................. 524/284
See application file for complete search history.

(56) References Cited

U.S. PATENT DOCUMENTS

| | | | | |
|---|---|---|---|---|
| 2,387,842 A | * | 10/1945 | Soltzberg | C07D 493/04 549/464 |
| 6,395,810 B1 | * | 5/2002 | Luitjes | C08K 5/1535 523/218 |
| 7,294,741 B2 | | 11/2007 | Bub et al. | |
| 8,258,325 B2 | | 9/2012 | Grass et al. | |
| 2003/0114635 A1 | * | 6/2003 | Van Es | C07D 493/04 528/274 |
| 2009/0301348 A1 | * | 12/2009 | Grass | C07D 493/04 106/287.2 |
| 2011/0196161 A1 | | 8/2011 | Fuertes et al. | |
| 2012/0116101 A1 | | 5/2012 | Fuertes et al. | |
| 2014/0088226 A1 | | 3/2014 | Gevers et al. | |
| 2014/0194648 A1 | | 7/2014 | Boeing et al. | |

FOREIGN PATENT DOCUMENTS

| | | |
|---|---|---|
| WO | WO 99/45060 A1 | 9/1999 |
| WO | WO 01/83488 A1 | 11/2001 |
| WO | WO 2006/103338 A1 | 10/2006 |
| WO | WO 2008/095571 A1 | 8/2008 |
| WO | WO 2008/155159 A1 | 12/2008 |
| WO | WO 2012/175237 A1 | 12/2012 |
| WO | WO 2013/092655 A1 | 6/2013 |

OTHER PUBLICATIONS

STN Search—Dec. 10, 2015.*
International Search Report issued Apr. 3, 2013 in PCT/EP2012/076064.
U.S. Appl. No. 14/367,730, filed Jun. 20, 2014, Grass, et al.

* cited by examiner

*Primary Examiner* — Ling Choi
*Assistant Examiner* — Ronald Grinsted
(74) *Attorney, Agent, or Firm* — Oblon, McClelland, Maier & Neustadt, L.L.P.

(57) ABSTRACT

An ester mixture of dianhydrohexitol, a composition comprising the ester mixture and a polymer composition comprising the ester mixture or the composition, the use thereof, and a process by which the ester mixture can be prepared, where the proportion of C8 based on the sum of C8 and C10 in the overall ester mixture is 45 mol % to 85 mol %.

17 Claims, No Drawings

DIANHYDROHEXITOL DIESTER MIXTURE GC

CROSS-REFERENCE TO RELATED APPLICATIONS

This application is a National Stage of PCT/EP2012/076064, which was filed on Dec. 19, 2012. This application is based upon and claims the benefit of priority to German Application No. 10 2011 089 495.0, which was filed on Dec. 21, 2011.

The present invention concerns an ester mixture of dianhydrohexitol, a composition comprising the ester mixture and a polymer composition comprising the ester mixture or the composition, the use thereof, and also a method whereby the ester mixture is obtainable.

The polymer composition may comprise for example polyvinyl chloride (PVC), polylactic acid (PLA), polyurethane or polyhydroxyalkanoates.

Polyvinyl chloride (PVC) is commercially one of the most important polymers. It is widely used both as rigid PVC and as flexible PVC.

Flexible PVC is produced by additizing the PVC with plasticizers, predominantly phthalic esters, in particular di-2-ethylhexyl phthalate (DEHP), diisononyl phthalate (DINP) and diisodecyl phthalate (DIDP). Existing and possibly future legislation regulating the usage of phthalates has created a need to find novel esters useful as plasticizers for PVC and other polymers.

U.S. Pat. No. 2,387,842 describes isomannide dibutyrate, isosorbide di(acetate/butyrate), isosorbide dihexanoate, isosorbide dioctanoate and isosorbide di-2-ethylhexanoate as useful PVC plasticizers. The corresponding flexible PVC test specimens were produced by use of solvents, i.e. under less than ideal industrial conditions. Preferred isosorbide esters were those obtained from mixtures of carboxylic acids. There should be 2 to 9 carbon atoms in the first carboxylic acid and 3 to 10 carbon atoms in the second one subject to the proviso that the sum of the carbon atoms should be at least 5 and not greater than 18.

WO 99/45060 describes inter alia C3-C11 alkanoates of isosorbide or of isomannide. Examples describe the synthesis of an isosorbide dioctanoate (IsDO) and also of the isosorbide esters based on butyric acid (IsDB), hexanoic acid (IsDH) and 2-ethylhexanoic acid (IsDEH) and report some performance characteristics in plasticized polymers (PVC and nitrocellulose).

WO 2001/083488 describes a method of producing anhydroglycitol esters, for example isosorbide esters, having improved colour, and postulates high conversions (98-100%) by using macroporous acidic ion exchangers as esterification catalyst. Corresponding diesters based on C3-C20 carboxylic acids were said to be advantageous for the process. Esters based on C6-C12 carboxylic acids were referred to as suitable for use as plasticizers. The synthesis of isosorbide di-n-octanoate (IsDO) and isosorbide di-2-ethylhexanoate (IsDEH) was exemplified.

WO2006/103338 describes a method of producing inter alia isosorbide esters by using a combination of two catalysts, one of which is hypophosphorous acid. This appears to give esters having better colour numbers and higher purities than described in WO2001/083488 for example. Again, only 2-ethylhexanoic acid and n-octanoic acid were explicitly referred to as carboxylic acids which can be reacted using this method.

WO 2008/095571 describes synthesis and use of mixtures of isosorbide esters obtainable by esterifying isomeric nonanoic acids (branched and linear) with isosorbide. However, plastisols based on this plasticizer have a significantly higher viscosity than that of the current standard plasticizer diisononyl phthalate (DINP), portending worse processability. Similarly, the glass transition temperatures are very significantly inferior to that of DINP.

The melting point of the pure isosorbide diester of n-octanoic acid is only just below room temperature, so using the ester at lower temperatures would be uncommercial in many processing methods of PVC plastisol technology.

The corresponding pure isosorbide di-n-decanoate even has a melting point above 35° C., and is largely incompatible with PVC.

The problem addressed by the present invention was that of finding a dianhydrohexitol-based diester or diester mixture having improved performance characteristics.

The problem is solved by an ester mixture as defined in Claim 1.

An ester mixture comprising a compound conforming to formula I:

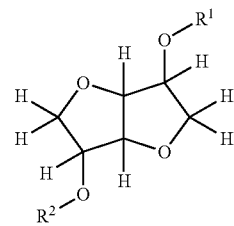

wherein $R^1$ and $R^2$ are each independently selected from: C8-alkyl linear, C8-alkyl branched, C8-alkene wherein said C8-alkene may be partially or completely epoxidized, C10-alkyl linear, C10-alkyl branched, C10-alkene wherein said C10-alkene may be partially or completely epoxidized, and wherein the carbon atom which binds the particular $R^1$ or $R^2$ moiety directly to the oxygen in formula I is linked via a double bond to a further oxygen atom, and wherein the proportion of C8 based on the sum of C8 and C10 in the entire ester mixture is in the range from 45 mol % to 85 mol %.

C8 or as the case may be C10 refers to the number of carbon atoms in the carbon chain.

The proportion of C10 in the ester mixture computes as the sum of C8 and C10 in the ester mixture (corresponds to 100 mol %) minus the proportion of C8.

For example, a mixture consisting to equal parts of pure C8-diester and pure C10-diester has a 50 mol % proportion of C8. But, for example, a pure C8/C10-ester, i.e. an ester wherein one alcohol group is esterified with C8 and the other alcohol group is esterified with C10, similarly also has a 50 mol % proportion of C8. The latter is also an ester mixture for the purposes of this invention.

"In the entire ester mixture" is to be understood as also comprehending those esters in the ester mixture which do not conform to formula I, for example monoesters of dianhydrohexitol which are present in the ester mixture. Following saponification of the entire ester mixture, all the C8-acids and all the C10-acids are captured separately and ratioed.

The C8/C10 ratio is captured via gas-chromatography analyses of the methyl esters of the corresponding fatty acids.

The number of different esters in the ester mixture is preferably at least two and more preferably at least three.

The ester mixture preferably comprises at least two esters that differ in their total number of carbon atoms. That is, for example, a C8,C8-ester and a C8,C10-ester.

In a further embodiment, the proportion of C8 based on the sum of C8 and C10 in the entire ester mixture is in the range from 45 mol % to 75 mol %.

In one embodiment, the doubly esterified alcohol is isosorbide.

In one embodiment, $R^1$ is selected from: C8-alkyl linear, C10-alkyl linear.

In a further embodiment, $R^2$ is selected from: C8-alkyl linear, C10-alkyl linear.

In a further embodiment, the ester mixture comprises a mixture of the following three compounds:

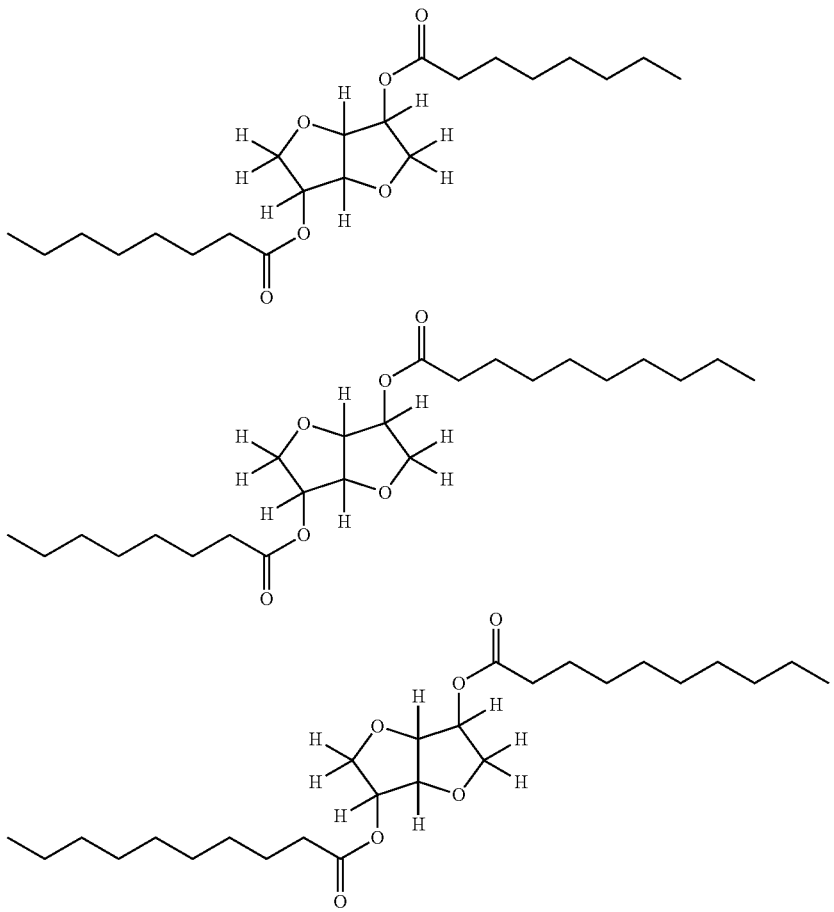

In a further embodiment, the proportion of C8 based on the sum of C8 and C10 in the entire ester mixture is in the range from 45 mol % to 65 mol %.

In a further embodiment, the proportion of C8 based on the sum of C8 and C10 in the entire ester mixture is in the range from 50 mol % to 65 mol %.

In a further embodiment, the sum of C8 and C10 has a proportion of above 50 mol % in the entire ester mixture based on all acid chains.

If the entire ester mixture is transesterified and the methyl esters resulting therefrom are all captured analytically, then the C8-acids and C10-acids together comprise an above 50 mol % proportion of the mixture of all acids.

The sum of C8 and C10 preferably has a proportion of above 60 mol % in the entire ester mixture based on all acid chains, more preferably above 70 mol % and most preferably above 80 mol %.

Formula I and its stereocentres preferably have the spatial structure of isosorbide.

A composition comprising the ester mixture is claimed as well as the ester mixture.

The composition comprises one of the ester mixtures described above, a high boiler and/or a low boiler.

The composition may also include two or more high boilers, i.e. a high-boiler mixture, and also two or more low boilers, i.e. a low-boiler mixture.

High boiler in connection with this invention is to be understood as meaning a compound with a boiling point above that of the C10,C10-ester. For example, high boilers have a higher retention time on an apolar column than the C10,C10-ester in a gas-chromatographic analysis of the composition.

High boilers can arise for example as a result of corresponding fractions of other carboxylic acids, for example C12 or C14, being present in the carboxylic acid mixture used for the reaction and C10,C12-esters or C10,C14-esters for example being formed as a consequence. High boilers can further be formed by partial ring-opening of the feed dianhydrohexitol to the monoanhydrohexitol with subsequent esterification to the corresponding di-, tri- or tetraesters of monoanhydrohexitol with the corresponding carboxylic acids.

Low boiler in connection with this invention is to be understood as meaning a compound with a boiling point below that of the C8,C8-ester.

For example, low boilers have a lower retention time on an apolar column than the C8,C8-ester in a gas-chromatographic analysis of the composition.

Low boilers can be the result for example of corresponding fractions of other, generally shorter-chain, carboxylic acids such as, for example, C6 or C4 being present in the carboxylic acid mixture used for the reaction and C6-C8-esters or C4-C8-esters for example also being formed as a consequence.

Low boilers can also be formed as a result of incompletely converted isosorbide esters (monoesters) remaining in the product or being formed for example by partial hydrolysis during the work-up after the reaction.

Technical-grade mixtures of fatty acids may contain for example not only shorter-chain but also longer-chain carboxylic acids, as is the case for example with so-called forerun fatty acids which are obtainable from palm kernel oil or coconut oil and are commercially available as Edenor V85 (from Emery) or C-810L (P&G Chemicals) for example.

In a further embodiment, the proportion of high boilers is less than 15 area % based on the ester signals of the composition.

In a further embodiment, the proportion of high boilers is less than 5 area % based on the ester signals of the composition.

In a further embodiment, the proportion of high boilers is less than 2.5 area % based on the ester signals of the composition.

A lower proportion of high boilers improves certain performance characteristics.

In a further embodiment, the proportion of low boilers is less than 4.5 area % based on the ester signals of the composition.

In a further embodiment, the proportion of low boilers is less than 2.5 area % based on the ester signals of the composition.

In a further embodiment, the proportion of low boilers is less than 1 area % based on the ester signals of the composition.

The area % proportions are determined using merely ester signals, i.e. low boilers and high boilers as per the above definition and the diester mixture itself; that is, solvent or carboxylic acid signals are not co-integrated.

A lower proportion of high boilers improves certain performance characteristics.

A further claim is to a polymer composition comprising one of the ester mixtures described above or one of the compositions described above. This polymer composition, in addition to the ester mixtures of the present invention, may also comprise one or more other plasticizers.

In one embodiment, the polymer composition comprises one of the ester mixtures described above and also a polymer.

The polymer preferably comprises polyvinyl chloride (PVC), polylactic acid (PLA), polyurethane or polyhydroxyalkanoates, more preferably PVC.

In a further embodiment, the polymer composition comprises one of the compositions described above and also a polymer.

The polymer preferably comprises polyvinyl chloride (PVC), polylactic acid (PLA), polyurethane or polyhydroxyalkanoates, more preferably PVC.

In addition to the ester mixture itself, the use thereof as a plasticizer is also claimed. Preferably as a plasticizer for a polymer, more preferably as a plasticizer for polyvinyl chloride (PVC).

The use of the composition as a plasticizer is also claimed. Preferably as a plasticizer for a polymer, more preferably as a plasticizer for polyvinyl chloride (PVC).

A further problem addressed was that of providing a method whereby a dianhydrohexitol-based diester or diester mixture having improved performance characteristics is obtainable.

This problem is solved by a method as defined in claim 13.

A method comprising the steps of
a) providing a dianhydrohexitol,
b) admixing n-octanoic acid and n-decanoic acid,
c) esterifying the acids of b) with the alcohol of a) in the presence of at least one catalyst,
d) terminating the esterifying reaction of c) as soon as the proportion of monoester has fallen below 2.0 area %.

It was surprisingly found that controlling the proportion of monoesters in the reaction mixture provides control over not only the proportion of low boilers but also the proportion of high boilers in the product mixture.

The proportion of monoesters which are low boilers rises significantly at the start of the reaction. The monoesters formed then react to form the diesters. At times the gas-chromatographically determined fraction of monoesters exceeds 25 area %.

The terminating in step d) is thus effected after the fraction of monoesters has first risen to beyond 2.0 area % and then, due to the further conversion to the diester in the later course of the reaction, there is a drop in the monoester fraction to below 2.0 area %.

The content level of low and high boilers can be determined by gas chromatography for example. In gas chromatography, high boilers have a higher retention time on an apolar column than the C10,C10-ester. Low boilers have a lower retention time on an apolar column than the C8,C8-ester. According to the present invention, the signals in the gas chromatogram are assigned using GC/MS analyses.

The area % proportions are determined using merely ester signals, i.e. low boilers and high boilers as per the above definition and the diester mixture itself; that is, solvent or carboxylic acid signals are not co-integrated.

Control over the product composition is achieved by terminating the reaction as the monoester content decreases to below a limiting value. This terminating the reaction is to be understood as meaning that the reaction mass is cooled down by more than 20 K from the previous setting of the reaction temperature. This cooling down can take the form of actively cooling or else be passive in that the heating element is switched off and no further heat is supplied.

This method is useful, for example, for obtaining the ester mixtures described above.

In one embodiment of the method, the dianhydrohexitol provided in step a) comprises isosorbide.

In one embodiment of the method, the terminating in step d) is effected as soon as the proportion of monoester has dropped below 1.6 area %.

This can be used to maintain the proportion of low boilers at a low value.

In one embodiment of the method, the terminating in step d) is effected as soon as the proportion of monoester has dropped below 1.0 area %.

This can be used to maintain the proportion of low boilers at a particularly low value.

In one embodiment of the method, the catalyst used in step c) is hypophosphorous acid.

This provides particularly good conversions, selectivities and colour numbers.

In a further embodiment, step c) utilizes a catalyst mixture which, in addition to hypophosphorous acid, may additionally also comprise acidic ion exchangers, sulfuric acid, toluenesulfonic acid, methanesulfonic acid or metal-containing catalysts such as, for example, tetraalkyl titanates.

In one embodiment of the method, the carboxylic acids in step b) comprise n-octanoic acid and n-decanoic acid.

The ester mixtures obtained by using these carboxylic acids have particularly good performance characteristics.

In one embodiment of the method, n-octanoic acid and n-decanoic acid are admixed in step b) in a molar ratio in the range from 85:15 and 45:55.

Using the carboxylic acids in this ratio provides ester mixtures having particularly good performance characteristics.

In one embodiment of the method, n-octanoic acid and n-decanoic acid are admixed in step b) in a molar ratio in the range from 80:20 and 45:55.

Using the carboxylic acids in this ratio provides ester mixtures having particularly good performance characteristics.

The ester mixtures obtainable by one of the methods described above are claimed as well as the method.

The ester mixtures obtained according to one of the methods described above are further claimed.

The use as plasticizers of the ester mixtures obtained or obtainable by this method is also claimed.

The invention will now be more particularly elucidated with working examples.

Preparing the Ester Mixture:

The method used can be used to esterify a dianhydrohexitol or a product comprising at least 95% by weight of dianhydrohexitol with the corresponding carboxylic acids in the presence or absence of a catalyst, preferably in the presence of hypophosphorous acid. The carboxylic acids or carboxylic acid mixture used to form the ester are preferably used in excess, preferably at a molar excess of 5 to 50 mol %, in particular 10 to 30 mol %, of the molar amount needed to form the diester.

The dianhydrohexitol compound used as starting material can be in particular an isosorbide. The isosorbide may comprise solid isosorbide or aqueous solutions of isosorbide.

To remove the water of reaction formed in the course of the esterification, the water of reaction can advantageously be distilled out of the reaction mixture together with the carboxylic acid(s). The carboxylic acid(s) thus serve as entrainer.

A possible method of esterification is described for example in WO2006/103338.

The comparative sample ISDIN-IS (to prepare recipe 2 in Table 2) was obtained as described in Examples 1 and 2 of WO2008/095571.

Ester mixtures 3 to 10, as discussed hereinbelow (cf. Table 1), were obtained as follows:

1.2 mol of isosorbide (from Cerestar), 2.8 mol of a defined C8/C10 fatty acid mixture (each from Sigma Aldrich) having a composition as per Table 1 and 0.015 mol of hypophosphorous acid (50% aqueous solution, from Sigma Aldrich) were initially charged to an esterification apparatus consisting of a 1 l multi-neck flask equipped with a stirrer, an immersion tube, a sampling stud, a thermometer and a water separator mounted with an intensive condenser (batches 3 to 10).

The apparatus was flushed with 6 l of $N_2$/hour per hour via the immersion tube before the start of the reaction. The reaction itself took place with nitrogen sparging. The reaction mixture was gradually temperature-regulated to 240° C. with stirring. A temperature of about 200° C. marked the onset of boiling. By-produced water at the onset of boiling was continuously removed from the reaction via the water separator. The esterification generated about 43 ml (2.4 mol) of water of reaction. The reaction time was about 4.5 hours.

The reaction was tracked by gas chromatography. The batch was discontinued as soon as the proportion of monoester had dropped below 2.0 area %.

For aftertreatment, the reaction effluent from the esterification was transferred into a 1 l flask which, following admixture of 2% by weight of activated carbon (CAP Super from Norit), was connected to a Claisen bridge with vacuum divider. An immersion tube with nitrogen terminus and a thermometer were fitted. Then, starting at 210° C. in vacuo (<40 mbar), the bulk of the excess acid was distilled off while the remaining acid was subsequently removed by stripping with nitrogen at 190 to 200° C. (in the course of about 2 hours). The reaction mass was subsequently cooled down to <90° C. and the flask was vented with nitrogen. The ester was filtered through a Büchner funnel with filter paper and precompacted filter cake of filter aid (D14 Perlite) via a suction bottle. The filtrate was subjected to a GC analysis.

Product 11 (cf. Table 1) was synthesized according to the following protocol:

2.5 mol of isosorbide (from Cerestar), 6.0 mol of a defined C8/C10 fatty acid mixture (each from Sigma Aldrich) as per number 11 in Table 1 and 0.034 mol of hypophosphorous acid (50% aqueous solution, from Sigma Aldrich) were initially charged to an esterification apparatus consisting of a 4 l multi-neck flask equipped with a stirrer, an immersion tube, a sampling stud, a thermometer and a water separator mounted with an intensive condenser.

The apparatus was flushed with 6 l of $N_2$/hour per hour via the immersion tube before the start of the reaction. The reaction itself took place with nitrogen sparging. The reaction mixture was gradually temperature-regulated to 240° C. with stirring. A temperature of about 192° C. marked the onset of boiling. By-produced water at the onset of boiling was continuously removed from the reaction via the water separator. The esterification generated about 90 ml (5.0 mol) of water of reaction. The reaction time was about 7 hours.

The reaction was tracked by gas chromatography. The batch was discontinued before the proportion of monoester had dropped below 2.0 area %.

For aftertreatment, the reaction effluent from the esterification was transferred into a 2 l flask which, following admixture of 2% by weight of activated carbon (CAP Super from Norit), was connected to a Claisen bridge with vacuum divider. An immersion tube with nitrogen terminus and a thermometer were fitted. Then, starting at 210° C. in vacuo (<40 mbar), the bulk of the excess acid was distilled off. The batch was cooled down to 100° C. in a stream of nitrogen by injection of water. The batch was dried in vacuo (<40 mbar) for 20 min and then vented with nitrogen.

The 4 times molar excess of 10% NaOH solution was added at 80° C., and stirring was continued under nitrogen sparging for a further 15 min. The batch was then heated to 180° C. in vacuo and mixed with a further 5% by weight of water to keep the steam distilling going. Further water was injected to reduce the reaction temperature to 130° C. The reaction mixture was subsequently dried in vacuo in a temperature range of 130-80° C. The ester was filtered through a Büchner funnel with filter paper and precompacted filter cake of filter aid (D14 Perlite) by vacuum in a suction bottle. The filtrate was subjected to a GC analysis.

Product 12 (cf. Table 1) was synthesized according to the following protocol:

1.5 mol of isosorbide (from Cerestar), 3.8 mol of a defined C8/C10 fatty acid mixture (each from Sigma Aldrich) as per number 12 in Table 1 and 0.020 mol of hypophosphorous acid (50% aqueous solution, from Sigma Aldrich) were initially charged to an esterification apparatus consisting of a 2 l multi-neck flask equipped with a stirrer, an immersion tube, a sampling stud, a thermometer and a water separator mounted with an intensive condenser.

The apparatus was flushed with 6 l of $N_2$/hour per hour via the immersion tube before the start of the reaction. The reaction itself took place with nitrogen sparging. The reaction mixture was gradually temperature-regulated to 240° C. with stirring. A temperature of about 200° C. marked the onset of boiling. By-produced water at the onset of boiling was continuously removed from the reaction via the water separator. The esterification generated about 53 ml (2.9 mol) of water of reaction. The reaction time was about 2.5 hours.

The reaction was tracked by gas chromatography. The reaction was discontinued before the proportion of monoester had dropped below 2.0 area %.

For aftertreatment, the reaction effluent from the esterification was transferred into a 2 l flask which, following admixture of 2% by weight of activated carbon (CAP Super from Norit), was connected to a Claisen bridge with vacuum divider. An immersion tube with nitrogen terminus and a thermometer were fitted. Then, starting at 210° C. in vacuo (<40 mbar), the bulk of the excess acid was distilled off while the remaining acid was subsequently removed by stripping with nitrogen at 190 to 200° C. (in the course of about 2 hours). The reaction mass was subsequently cooled down to <90° C. and the flask was vented with nitrogen. 2% by weight of $Al_2O_3$ was then added to the reaction mixture which was stirred for 60 min at around 80° C. The ester was filtered through a Büchner funnel with filter paper and precompacted filter cake of filter aid (D14 Perlite) via a suction bottle. The filtrate was subjected to a GC analysis.

Product 13 (cf. Table 1) was synthesized according to the following protocol:

1.5 mol of isosorbide (from Cerestar), 6.0 mol of a defined C8/C10 fatty acid mixture (each from Sigma Aldrich) as per number 13 in Table 1 and 0.011 mol of sulfuric acid (95-97% strength, from Sigma Aldrich) were initially charged to an esterification apparatus consisting of a 2 l multi-neck flask equipped with a stirrer, an immersion tube, a sampling stud, a thermometer and a water separator mounted with an intensive condenser (batch 13).

The apparatus was flushed with 6 l of $N_2$/hour per hour via the immersion tube before the start of the reaction. The reaction itself took place with nitrogen sparging. The reaction mixture was gradually temperature-regulated to 180° C. with stirring. By-produced water at the onset of boiling was continuously removed from the reaction via the water separator. The esterification generated about 58 ml (3.2 mol) of water of reaction.

The reaction was tracked by gas chromatography. The batch was not discontinued when the proportion of monoester had dropped below 2.0 area %, and not even when the proportion of monoester had dropped to below 1.0 area %.

The reaction time was about 15 hours. Thereafter, the reaction was terminated and the proportion of high and low boilers was again determined (see Table 1).

For aftertreatment, the reaction effluent from the esterification was transferred into a 2 l flask which, following admixture of 2% by weight of activated carbon (CAP Super from Norit), was connected to a Claisen bridge with vacuum divider. An immersion tube with nitrogen terminus and a thermometer were fitted. Then, starting at 210° C. in vacuo (<40 mbar), the bulk of the excess acid was distilled off while the remaining acid was subsequently removed by stripping with nitrogen at 190 to 200° C. (in the course of about 2 hours). The reaction mass was subsequently cooled down to <90° C. and the flask was vented with nitrogen.

The ester was filtered through a Büchner funnel with filter paper and precompacted filter cake of filter aid (D14 Perlite) via a suction bottle. The filtrate was subjected to a GC analysis.

Product 14 (cf. Table 1) was synthesized according to the following protocol:

1.5 mol of sorbitol (from Cerestar), 3.8 mol of a defined C8/C10 fatty acid mixture (each from Sigma Aldrich) as per number 14 in Table 1 and 46.25 g of Amberlyst 46 (from Sigma Rohm & Haas) were initially charged to an esterification apparatus consisting of a 2 l multi-neck flask equipped with a stirrer, an immersion tube, a sampling stud, a thermometer and a water separator mounted with an intensive condenser.

The apparatus was flushed with 6 l of $N_2$/hour per hour via the immersion tube before the start of the reaction. The reaction itself took place with nitrogen sparging. The reaction mixture was gradually temperature-regulated to 145° C. with stirring. By-produced water at the onset of boiling was continuously removed from the reaction via the water separator. Esterification and ring closure generated about 110 ml (6.1 mol) of water of reaction.

The reaction was tracked by gas chromatography. The batch was not discontinued when the proportion of monoester had dropped below 2.0 area %, and not even when the proportion of monoester had dropped to below 1.0 area %.

The reaction time was about 8 hours. The aim of this synthesis was to generate a large proportion of high boilers.

For aftertreatment, the reaction effluent from the esterification was transferred into a 2 l flask which, following admixture of 2% by weight of activated carbon (CAP Super from Norit), was connected to a Claisen bridge with vacuum divider. An immersion tube with nitrogen terminus and a thermometer were fitted. Then, starting at 210° C. in vacuo (<40 mbar), the bulk of the excess acid was distilled off while the remaining acid was subsequently removed by stripping with nitrogen at 190 to 200° C. (in the course of about 2 hours). The reaction mass was subsequently cooled down to <90° C. and the flask was vented with nitrogen.

The ester was filtered through a Büchner funnel with filter paper and precompacted filter cake of filter aid (D14 Perlite) via a suction bottle. The filtrate was subjected to a GC analysis.

Characterizing the Ester Mixture as Regards the C8/C10 Ratio (Analysis):

Procedure for Fatty Acid Analysis after Transesterification to the Methyl Ester

The C8/C10 ratio of the fatty acids in dianhydrohexitol di-fatty acid esters can be determined by transesterification to the methyl esters and subsequent gas-chromatographic measurements.

The samples were worked up in accordance with Ph. Eur. 01/2008:20422 corrected 6.8 Method C (fatty acid assay in polysorbate) and compared with the test mixtures described there. Sample preparation procedure was as follows:

0.1 g of sample was admixed with 2.0 ml of NaOH solution (20 g of NaOH/l of anhydrous methanol) and refluxed for 30 minutes. Then, 2.0 ml of methanolic boron trifluoride solution (140 mg/ml) were added before refluxing for a further 30 minutes.

Following admixture of 4.0 ml of n-heptane the reaction solution was refluxed for a further 5 minutes and then cooled down to room temperature. The organic phase was extracted once with 10 ml of saturated sodium chloride solution and then a further three times with 2.0 ml of Milli-Q water. The organic phase was dried over about 0.2 g of anhydrous sodium sulfate. The upper clear phase was used for analysis.

GC analysis was performed with the parameters as follows:

capillary column: 30 m DB-WAX, 0.32 mm ID, 0.5 µm film
carrier gas: helium
column head pressure: 100 kPa
split: about 100 ml/min
oven temperature: 80° C.-10° C./min-220° C. (40 min)
injector: 250° C.
detector (FID): 250° C.
injection volume: 1.0 µl The components in the sample chromatogram were identified using a comparative solution of the relevant fatty acid methyl esters. In this case, the methyl esters here are those of caproic acid, caprylic acid, capric acid, lauric acid and myristic acid. The signals in the sample chromatogram were subsequently standardized to 100 area %.

The mass ratio was computed using a computed response factor between the C8 and C10 fatty acid methyl ester and standardization of the two components to 100%. This gives the C8/C10 ratio as standardized % by mass.

The standardized mass percent ratio was subsequently arithmetically converted into a standardized mol % ratio.

The method described above was used to obtain ester mixtures wherein n-octanoic acid and n-decanoic acid were used as reactants in the following molar ratios: 85:15, 75:25, 65:35, 58:42, 57:43, 50:50, 40:60, 25:75.

The products obtained from the synthesis and also the pure isosorbide 2,5-dioctanoate ester and the pure isosorbide 2,5-didecanoate ester were each analysed by the procedure described above to determine the fatty acid distribution. The results are summarized below in Table 1.

TABLE 1

Feed ratio and product composition of recited isosorbide diesters.

| No. | C8 proportion of feed [mol %] | C10 proportion of feed [mol %] | Low boilers [area %] | Diesters [area %] | High boilers [area %] | C8/C10 ratio by GC after saponification [area %] | C8/C10 ratio by GC after saponification [standardized % by mass] | C8/C10 ratio by GC after saponification [standardized mol %] |
|---|---|---|---|---|---|---|---|---|
| — | 100 | 0 | 0.20 | 98.74 | 1.05 | 99.9/0.0 | 100.0/0.0 | 100.0/0.0 |
| 3 | 85 | 15 | 0.39 | 98.90 | 0.71 | 79.9/19.8 | 83.0/17.0 | 85.4/14.6 |
| 4 | 75 | 25 | 0.26 | 98.92 | 0.81 | 68.0/31.8 | 72.1/27.9 | 75.5/24.5 |
| 5 | 65 | 35 | 0.26 | 99.18 | 0.52 | 58.0/42.0 | 62.6/37.4 | 66.7/33.3 |
| 6 | 58 | 42 | 0.23 | 99.08 | 0.69 | 48.3/51.5 | 53.2/46.8 | 57.6/42.4 |
| 7 | 57 | 43 | 0.18 | 98.67 | 1.04 | 47.9/51.8 | 52.8/47.2 | 57.2/42.8 |
| 8 | 50 | 50 | 0.26 | 99.33 | 0.40 | 42.8/56.9 | 47.6/52.4 | 52.0/48.0 |
| 9 | 40 | 60 | 0.38 | 99.28 | 0.34 | 32.9/66.9 | 37.3/62.7 | 41.5/58.5 |
| 10 | 25 | 75 | 0.29 | 99.56 | 0.14 | 19.9/79.6 | 23.2/76.8 | 26.5/73.5 |
| — | 0 | 100 | 0.39 | 99.53 | 0.08 | 0.2/99.4 | 0.0/100 | 0.0/100.0 |
| 11 | 57 | 43 | 2.2 | 97.3 | 0.5 | 53.0/46.2 | 58.1/41.9 | 62.4/37.6 |
| 12 | 57 | 43 | 4.6 | 95.0 | 0.4 | 52.7/46.2 | 58.0/42.0 | 62.3/37.7 |
| 13 | 57 | 43 | 0.1 | 94.8 | 5.0 | 53.4/45.2 | 58.9/41.1 | 63.1/36.9 |
| 14 | 57 | 43 | 0.3 | 74.3 | 25.5 | 53.8/45.0 | 59.1/40.9 | 63.3/36.7 |

All samples were also measured for their Hazen colour number (APHA). It was found to be below 40 for the samples up to 12 inclusive. It was 160 for sample 13 and 433 for sample 14. The values above 80 are undesirable, since they deliver significantly discoloured products.

Comparative Tests for Plastisol Application:
1. Production of Plastisol

The PVC plastisol produced was of the type which is used, for example, to fabricate topcoat films for floor coverings. The particulars in the plastisol recipes are each in weight fractions. The PVC used was Vestolit B 7021-Ultra. The comparative substances used were diisononyl phthalate (DINP, VESTINOL 9 from Evonik Industries) and the isosorbide diester based on isononanoic acid (ISDIN-IS). The recipes of the polymer compositions are listed in Table 2.

TABLE 2

| | Recipe: | | | | | | | | | |
|---|---|---|---|---|---|---|---|---|---|---|
| Additive-Charge: | 1 | 2 | 3* | 4* | 5* | 6* | 7* | 8* | 9 | 10 |
| B 7021-Ultra | 100 | 100 | 100 | 100 | 100 | 100 | 100 | 100 | 100 | 100 |
| DINP | 50 | | | | | | | | | |
| ISDIN-IS | | 50 | | | | | | | | |
| C8:C10 = 85:15 | | | 50 | | | | | | | |
| C8:C10 = 75:25 | | | | 50 | | | | | | |
| C8:C10 = 65:35 | | | | | 50 | | | | | |
| C8:C10 = 58:42 | | | | | | 50 | | | | |
| C8:C10 = 57:43 | | | | | | | 50 | | | |
| C8:C10 = 50:50 | | | | | | | | 50 | | |
| C8:C10 = 40:60 | | | | | | | | | 50 | |
| C8:C10 = 25:75 | | | | | | | | | | 50 |
| Drapex 39 | 3 | 3 | 3 | 3 | 3 | 3 | 3 | 3 | 3 | 3 |
| Mark CZ 149 | 2 | 2 | 2 | 2 | 2 | 2 | 2 | 2 | 2 | 2 |

*polymer composition according to the invention

The C8/C10 ratio used to synthesize the ester mixture is reported for samples 3 to 10 in column 1 of Table 2. The values accordingly correlate with columns 2 and 3 of Table 1. The resultant composition in the ester mixture obtained can be seen in the last column of Table 1.

In addition to the 50 parts by weight of plasticizer, every recipe further contains 3 parts by weight of an epoxidized soya bean oil as co-stabilizer (Drapex 39, from Galata), and also 2 parts by weight of a Ca/Zn-based thermal stabilizer (Mark CZ 149, from Galata).

The plasticizers were conditioned to 25° C. prior to addition. The constituents were weighed into a PE beaker, first the liquid ones and then the pulverulent ones. The mixture was hand mixed with a paste spatula until no unwetted powder remained. The mixing beaker was then clamped into the clamping apparatus of a dissolver stirrer. Prior to immersion of the stirrer into the mixture, the rotation rate was set to 1800 revolutions per minute. Once the stirrer had been switched on, stirring was continued until the temperature on the digital display of the thermosensor reached 30.0° C. This ensured that homogenization of the plastisol was achieved with a defined energy input. The plastisol was thereafter immediately conditioned at 25.0° C.

2. Measurement of Plastisol Viscosities

The viscosities of the PVC plastisols were measured using a Physica MCR 101 instrument (from Anton-Paar) in the rotation mode and with the measurement system "CC27".

The plastisol was initially homogenized once more in the mixing vessel by stirring with a spatula, then filled into the measurement system and measured isothermally at 25° C. The following points were targeted during the measurement:

1. A pre-shear of 100 $s^{-1}$ for a period of 60 s, during which no measured values were recorded (to even out any thixotropic effects).

2. A downward shear-rate progression starting at 200 $s^{-1}$ and ending at 0.1 $s^{-1}$, divided into a logarithmic series of 30 steps each of 5 seconds duration.

The measurements were as a rule (unless otherwise stated) carried out following a 24 h storage/ripening period for the plastisols. The plastisols were stored at 25° C. between the measurements.

Table 3 below shows the viscosity of each PVC paste at a shear rate of 100 $s^{-1}$. Paste number correlates with the recipe number in Table 2.

3. Gelling Behaviour

The gelling behaviour of the pastes was studied in a Physica MCR 101 in oscillation mode using a plate-on-plate measurement system (PP25), operated with shear-stress control. An additional temperature-regulating hood was attached to the equipment in order to homogenize heat distribution and achieve a uniform sample temperature.

The settings for the parameters were as follows:
Mode: temperature gradient
starting temperature: 25° C.
final temperature: 180° C.
heating/cooling rate: 5° C./min
oscillation frequency: 4-0.1 Hz ramp logarithmic
angular frequency omega: 10 1/s
number of measurement points: 63
measurement-point duration: 0.5 min
automatic gap adjustment F: 0 N
constant measurement-point duration
gap width: 0.5 mm
Measurement Procedure:

A spatula was used to apply a drop of the paste to be measured, free from air bubbles, to the lower plate of the measurement system. Care was taken here to ensure that some paste could exude uniformly out of the measurement system (although not more than about 6 mm overall) after the measurement system had been closed. The temperature-regulating hood was then positioned over the specimen and the measurement was started. The so-called complex viscosity of the paste was determined as a function of the temperature. Since a certain temperature is attained within a time span (determined by the heating rate of 5° C./min), information is obtained about the gelling rate of the measured system as well as about its gelling temperature. The onset of the gelling process was discernible in a sudden marked rise in the complex viscosity. The earlier the onset of this viscosity rise, the better the gellability of the system.

The measured curves obtained were used to determine the cross-over temperature. This procedure computes the point of intersection for the two y-variables chosen. The procedure is used to find the end of the linear viscoelastic region in an amplitude sweep (y: G', G"; x: gamma) in order to find the

TABLE 3

| paste number | 1 | 2 | 3 | 4 | 5 | 6 | 7 | 8 | 9 | 10 |
|---|---|---|---|---|---|---|---|---|---|---|
| paste viscosity after 24 h (100 s-1 ) | 5.73 | 10.8 | 6.32 | 6.60 | 6.64 | 6.68 | 6.77 | 6.84 | 6.99 | 7.35 |

Comparing the pastes, the pastes formed from the inventive polymer compositions (3, 4, 5, 6, 7, 8) have a significantly lower paste viscosity than the paste comprising ISDIN-IS (paste number 2). Using purely ISDIN-IS (non-inventive polymer composition 2) it is virtually impossible to produce a readily processable PVC paste, since its paste viscosity is very high.

crossing frequency in a frequency sweep (y: G', G"; x: frequency) or to ascertain the gel time or cure temperature (y: G', G"; x: time or temperature). The cross-over temperature documented here corresponds to the temperature of the first intersection of G' and G".

The results are shown in Table 4. Paste number correlates with the recipe number in Table 2.

TABLE 4

| paste number | 1 | 2 | 3 | 4 | 5 | 6 | 7 | 8 | 9 | 10 |
|---|---|---|---|---|---|---|---|---|---|---|
| cross-over temperature ° C. | 75.4 | 76.4 | 70.5 | 71.2 | 72.8 | 73.6 | 72.7 | 72.6 | 74.9 | 75.8 |

PVC pastes based on an inventive polymer composition versus a similar paste based on an isosorbide ester of isononanoic acid have, irrespective of the shear rate, a lower shear viscosity and hence an improved processability.

Gelling Behaviour:

Compared with the paste which contains ISDIN-IS (paste number 2), the pastes which contain an inventive polymer composition (paste numbers 3 to 8) exhibit significantly faster gelling. The gelling of pastes 3 to 8 is also faster than the gelling of pastes 9 and 10 and also of paste 1, which comprises the existing industry standard DINP.

4. Melting Points of Purely Ester Mixtures

Melting points were determined using Differential Scanning Calorimetry (DSC), in each case on the basis of the signal for the onset of melting. In the case of two or more melting points, the highest melting point was reported, since the first crystallizations ensue below this temperature.

The results are shown in Table 5. Plasticizer number correlates with the recipe number in Table 2.

TABLE 5

| plasticizer number | 1 | 2 | 3 | 4 | 5 | 6 | 7 | 8 | 9 | 10 |
|---|---|---|---|---|---|---|---|---|---|---|
| temperature ° C. | n.d. | n.d. | 7 | 3 | 3 | 5 | 5 | 7.5 | 13 | 22 | n.d. = not determinable

No melting point could be determined for plasticizer numbers 1 and 2. These substances merely exhibit a glass transition, since they are amorphous.

All melting points above 10° C. fail to satisfy the criteria for a plasticizer to be readily employable in large-scale industrial processes, since the products otherwise would have to be excessively heated at cold times of the year, which would lead to very high energy costs in order to ensure adequate flowability. Excessive heating could also induce premature gelling of the pastes even during the mixing operation, combined with a pronounced tendency to thicken, and hence significantly compromised processability.

Isosorbide esters with exclusively C8-acid or C10-acid have a comparatively high melting point and are accordingly economically unviable for plastisol methods (this corresponds to about one third of all commercial applications) for the abovementioned reasons. The C8/C10 mixtures all without exception have lower melting points and are accordingly significantly more suitable.

Avoidance of High Boilers

The formation of large proportions of high boilers leads to a significantly comprised performance of the plasticizer, specifically as regards processability (gelling) and efficiency (Shore hardness). To reduce the content level of high boilers in the product mixture, the method of the present invention provides that the esterification reaction be tracked by gas chromatography.

High boilers can form for example at high temperatures combined with long reaction times or on using certain mineral acids, for example sulfuric acid or sulfonic acids. This can lead to ring opening on the part of the dianhydrohexitol, or the corresponding mono- or diester, to form the monoanhydrohexitol or the corresponding esters. The excess of fatty acids can then lead to formation of di-, tri- and tetraesters of monoanhydrohexitol. The reaction is accordingly terminated as soon as the proportion of monoesters drops below a certain value in gas-chromatographic measurements.

It was surprisingly found that the proportion of monoesters in the reaction mixture provides good control of the proportion of high boilers in the product mixture.

Avoidance of Low Boilers

The formation of low boilers leads even at low mass fractions to a deterioration in plasticizer performance, specifically its extraction in water and its volatility. The monoesters are one example of such low boilers.

As noted in connection with high boilers, long reaction times can lead to the formation of high boilers. A drastically reduced reaction time, however, leads to reduced conversions and hence to fatty acid monoesters of dianhydrohexitol which are low boilers. Temperature and reaction time therefore have to be optimized so as to achieve the highest possible conversion of dianhydrosorbitol and monoester while at the same time avoiding the formation of high boilers to any significant extent. This was achieved by terminating the reaction as soon as the proportion of monoesters had dropped below a certain value in gas-chromatographic measurements.

Characterizing the Ester Mixture as Regards Low and High Boiler Content (Analysis):

The content level of low and high boilers was determined by gas chromatography. High boilers have a higher retention time on an apolar column than the C10,C10-ester. Low boilers have a lower retention time on an apolar column than the C8,C8-ester. According to the present invention, the signals in the gas chromatogram are assigned using GC/MS analyses. To record the gas-chromatographic spectra, for example, 0.1 g of sample was dissolved in 1.5 ml of acetone and transferred into a GC vial.

The gas-chromatographic analyses can in principle be carried out using any commercially available GC instrument equipped with the suitable apolar column. An Agilent instrument of the 6890 N type was used for the present gas-chromatographic analyses. The temperature of the oven was maintained at 120° C. for 1.4 min, then raised to 350° C. at a heating rate of 12.5 K/min and maintained at 350° C. for a further 17 min. The gas-chromatographic spectra were recorded using an Agilent HP5 column, via an FID detector, with helium as carrier gas. Other commercially available GC instruments operated with the same operating parameters gave comparable results. In this case, too, the signals have to be assigned once via GC/MS measurements.

The retention time range of the dianhydrohexitol fatty acid esters is between 15 and 22 min in the example under consideration. The low boilers are detected at between 6 and 15 min and the high boilers at between 22 and 32 minutes.

The area % proportions are determined using merely ester signals, i.e. low boilers and high boilers as per the above definition and the diester mixture itself; that is, solvent or carboxylic acid signals are not co-integrated.

Comparative Tests for Plastisol Application:

1. Production of Plastisol

The PVC plastisol produced was of the type which is used, for example, to fabricate topcoat films for floor coverings. The particulars in the plastisol recipes are each in weight fractions. The PVC used was Vestolit B 7021-Ultra. C8:C10 denotes the n-octanoic acid to n-decanoic acid ratio in which these reactants were used in the synthesis. The recipes of the polymer compositions are listed in Table 6. Recipe number correlates with the number in the first column of Table 1.

TABLE 6

Recipes for plastisol production

| | recipe: | | | | |
|---|---|---|---|---|---|
| Additive -- Charge: | 7* | 11 | 12 | 13 | 14 |
| B 7021 -- Ultra | 100 | 100 | 100 | 100 | 100 |
| C8:C10 = 57:43 | 50 | | | | |
| C8:C10 = 57:43 | | 50 | | | |
| C8:C10 = 57:43 | | | 50 | | |

TABLE 6-continued

Recipes for plastisol production

| | recipe: | | | | |
|---|---|---|---|---|---|
| Additive -- Charge: | 7* | 11 | 12 | 13 | 14 |
| C8:C10 = 57:43 | | | | 50 | |
| C8:C10 = 57:43 | | | | | 50 |
| Drapex 39 | 3 | 3 | 3 | 3 | 3 |
| Mark CZ 149 | 2 | 2 | 2 | 2 | 2 |

*polymer composition comprising an ester mixture obtained by a method according to the present invention In addition to the 50 parts by weight of plasticizer, every recipe further contains 3 parts by weight of an epoxidized soya bean oil as co-stabilizer (Drapex 39), and also 2 parts by weight of a Ca/Zn-based thermal stabilizer (Mark CZ 149).

The ester mixtures were conditioned to 25° C. prior to addition. The constituents were weighed into a PE beaker, first the liquid ones and then the pulverulent ones. The mixture was hand mixed with a paste spatula until no unwetted powder remained. The mixing beaker was then clamped into the clamping apparatus of a dissolver stirrer. Prior to immersion of the stirrer into the mixture, the rotation rate was set to 1800 revolutions per minute. Once the stirrer had been switched on, stirring was continued until the temperature on the digital display of the thermosensor reached 30.0° C. This ensured that homogenization of the plastisol was achieved with a defined energy input. The plastisol was thereafter immediately conditioned at 25.0° C.

2. Volatility

Plasticizer volatility was determined using an HB 43-S halogen dryer from Mettler Toledo. An empty clean aluminium dish was placed in the weighing pan prior to measurement. Thereafter, the aluminium dish was tared with a fibrous nonwoven web and about five grams of plasticizer were pipetted onto the fibrous nonwoven web and weighed.

The heating module was closed to start the measurement and the sample was heated at the maximum heating rate (pre-set) from room temperature to 200° C. and every 30 seconds the loss of mass at that point due to evaporation was automatically determined by weighing. After 10 min the measurement was automatically ended by the instrument.

A duplicate determination was carried out for every sample.

The results are shown in Table 7. Plasticizer number correlates with the recipe number in Table 6.

TABLE 7

| | Plasticizer number | | | | |
|---|---|---|---|---|---|
| | 7 | 11 | 12 | 13 | 14 |
| loss of mass [%] | 3.50 | 3.71 | 4.55 | 2.69 | 2.71 |

The polymer composition comprising an ester mixture obtained by a non-inventive method (plasticizer No. 12) gives a significantly higher loss of mass than polymer compositions comprising an ester mixture obtained by an inventive method (plasticizer numbers 7, 11, 13).

3. Water Resistance

Ageing resistance under various ambient conditions is a further essential quality criterion for PVC plasticizers. Especially the behaviour with regard to water (water imbibition & leachability of recipe constituents) and with regard to elevated temperatures (evaporation of recipe constituents & thermal ageing) offers an insight into ageing resistance.

If a plastic article imbibes water to a major degree, this changes not only the materials properties thereof but also its visual appearance (e.g. haze). High water imbibition is accordingly undesirable in general. Leachability is an additional criterion for setting the durability of formulation constituents under service conditions. This holds particularly for stabilizers, plasticizers and/or constituents thereof, since any reduction in the concentration of these recipe constituents in the plastic article can not only worsen the materials properties but also drastically shorten the useful life.

Water resistance was determined using fully gelled 1 mm polymer films of the corresponding plastisols (gelling conditions in Mathis oven: 200° C./2 min). The test specimens used were roundels 3 cm in diameter cut out of the films. Before being lodged in water, the test specimens were stored in a desiccator containing a drier (KC drying beads from BASF SE) at 25° C. for 24 hours. The initial weight was determined with an analytical balance to an accuracy of 0.1 mg. The test specimens were then stored in a shaker bath (of the WNB 22 type with "CDP" Peltier cooling, from Memmert GmbH) filled with completely ion-free water at a temperature of 30° C. for 7 days under the water surface with sample holders while being continuously agitated.

After lodgement, the roundels were removed from the water bath, dried off and weighed (=weight after 7 days). The difference from the initial weight was used to compute the water imbibition. After being reweighed, the test specimens were again stored for 24 hours at 25° C. in a desiccator containing a drier (KC drying beads) and then once more reweighed (final reweighing=weight after drying). The difference from the initial weight before water lodgement was used to compute the percentage loss of mass due to water lodgement (corresponds to loss by leaching).

The results are shown in Table 8. Test specimen number correlates with the recipe number in Table 6.

TABLE 8

| | test specimen number | | | | |
|---|---|---|---|---|---|
| | 7 | 11 | 12 | 13 | 14 |
| loss of mass [%] | −0.05 | −0.55 | −1.08 | −0.02 | −0.19 |

The mass lost by test specimen 11 is slightly up compared with the mass lost by test specimen 7, while that of test specimen 12 (having a high low-boiler content) is significantly up.

Significantly increased losses of mass severely limit the utility of plasticizers.

4. Plasticizing Effect

Its Shore hardness is a measure of the softness of a test specimen. The further a standardized needle is able to penetrate into the test specimen during a certain period of measurement, the lower the measured value obtained. The plasticizer with the highest efficiency produces the lowest value of Shore hardness for the same amount of plasticizer. Since formulations/recipes are in practice frequently standardized/optimized to a certain Shore hardness, accordingly, very efficient plasticizers make it possible to save a certain proportion in the recipe, and this represents a cost reduction for the processor.

To determine the Shore hardnesses, the pastes obtained as described above were poured into round brass moulds 42 mm in diameter (weight poured into mould: 20.0 g). The pastes in the moulds were then gelled at 200° C. in a circulating air drying cabinet for 30 min, removed after cooling and stored for at least 24 hours in a conditioning cabinet (25° C.) before measurement. Disc thickness was about 12 mm.

The hardness measurements were carried out to DIN 53 505 using a Shore A meter from Zwick-Roell, the measured value being read off after 3 seconds in each case. Measurements were carried out at three different places on each test specimen and averaged.

The results are shown in Table 9. Test specimen number correlates with the recipe number in Tables 2 and/or 6.

TABLE 9

| | test specimen number | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Shore A | 80 | 84 | 80 | 81 | 80 | 82 | 82 | 82 | 82 | 83 | 83 | 82 | 83 | 88 |

Compared with test specimen 2, which contains isosorbide esters based on isononanoic acid (ISDIN-IS) as plasticizer, test specimens 3-10 and 11-13 exhibit a lower Shore A hardness, i.e. greater "softness". The method of the present invention thus delivers ester mixtures that have a better efficiency in PVC mixtures than ISDIN-IS has. Plasticizer can accordingly be thereby saved, which leads to lower recipe costs. Recipe 14, comprising an ester mixture obtained by a non-inventive method, has a significantly higher Shore hardness.

Foams

The invention further claims the use in foams of an ester mixture according to the invention.

Many PVC articles are typically made to include layers of foam in order that the weight of the products and thus also the costs may be reduced by virtue of the lower material requirements. Floorings, wall coverings or artificial leathers are exemplary fields of use here. The user of a foamed product can benefit from superior structureborne sound insulation in the case of floor coverings for example.

The quality of foaming depends on many components within the formulation in that the type of PVC used and the plasticizer play an important part as well as the type and amount of foam former used. Plasticizers must accordingly deliver foamable compositions that are of low volatility, and allow faster processing at lower temperatures.

A foamable composition contains in general a polymer selected from the group consisting of polyvinyl chloride, polyvinylidene chloride, polyvinyl butyrate, polyalkyl methacrylate and copolymers, a foam former and/or foam stabilizer and a plasticizer.

EXAMPLE F1

Production of Expandable/Foamable PVC Plastisols (without Filler and/or Pigment)

The advantages of a plastisol according to the present invention will now be illustrated using a thermally expandable PVC plastisol that contains no filler and no pigment. The below plastisol according to the present invention is inter alia exemplary of thermally expandable plastisols used in the production of floor coverings. More particularly, the below plastisols according to the present invention are exemplary of foam layers used as back-side foams in PVC floorings of multilayered construction. The formulations presented are couched in general terms, and can/have to be adapted by a person skilled in the art to the specific processing and service requirements applicable in the particular use sector.

TABLE 10

Composition of expandable PVC plastisols from Example F1. [All particulars in parts by mass]

| plastisol recipe (Example F1) | 1** | 7* |
|---|---|---|
| Vinnolit MP 6852 | 100 | 100 |
| VESTINOL ® 9 | 59 | |
| isosorbide ester (No. 7) | | 59 |
| Unifoam AZ Ultra 7043 | 3 | 3 |
| zinc oxide | 2 | 2 |

**comparative example
*inventive example

The materials and substances used are more particularly elucidated in what follows:

Vinnolit MP 6852: microsuspension PVC (homopolymer) with K-value (as per DIN EN ISO 1628-2) of 68; from Vinnolit GmbH & Co KG.

VESTINOL® 9: diisononyl (ortho)phthalate (DINP), plasticizer; from Evonik Industries AG. isosorbide ester: dianhydrohexitol fatty acid diester with a composition as per compound No. 7 in Table 1.

Unifoam AZ Ultra 7043: azodicarbonamide, thermally activatable blowing agent; from Hebron S.A.

zinc oxide: ZnO, decomposition catalyst for thermal blowing agent, lowers the inherent decomposition temperature of the blowing agent, also acts as stabilizer, "Zinkoxid Aktiv®"; from Lanxess AG. The zinc oxide was premixed with a sufficient portion (1 phr) of the particular plasticizer used and then added.

Liquid and solid constituents of the formulation were weighed separately into a suitable PE beaker for each. The mixture was hand stirred with a paste spatula until no unwetted powder was left. The plastisols were mixed using a VDKV30-3 Kreiss dissolver (from Niemann). The mixing beaker was clamped into the clamping device of the dissolver stirrer. A mixer disc (toothed disc, finely toothed, Ø: 50 mm) was used to homogenize the sample. For this, the dissolver speed was raised continuously from 330 rpm to 2000 rpm, and stirring was continued until the temperature on the digital display of the thermosensor reached 30.0° C. (temperature increase due to friction energy/energy dissipation; see for example N. P. Cheremisinoff: "An Introduction to Polymer Rheology and Processing"; CRC Press; London; 1993). It was accordingly ensured that the plastisol was homogenized with a defined energy input. Thereafter, the plastisol was immediately conditioned at 25.0° C.

EXAMPLE F2

Production of Foam Foils and Determination of Expansion/Foaming Behaviour at 200° C. of Thermally Expandable Plastisols Obtained in Example F1

1. Production of Foam Foils and Determination of Expansion Rate

Foaming behaviour was determined using a thickness gauge suitable for flexible-PVC measurements (KXL047, from Mitutoyo) to an accuracy of 0.01 mm. A Mathis Labcoater (type: LTE-TS, manufacturer: W. Mathis AG) was used for foil production after adjustment of the roll blade to a blade gap of 1 mm. This blade gap was checked with a feeler gauge and adjusted if necessary. The plastisols were coated with the roll blade of the Mathis Labcoater onto a release paper (Warran Release Paper, from Sappi Ltd.) stretched flat in a frame. To be able to compute percentage foaming, first an incipiently gelled and unfoamed foil was produced at 200° C./30 seconds' residence time. The thickness of this foil (=initial thickness) was in all cases between 0.74 and 0.77 mm at the stated blade gap. The thickness was measured at three different places on the foil.

Foamed foils (foams) were then likewise produced with/in the Mathis Labcoater at 4 different oven residence times (60 s, 90 s, 120 s and 150 s). After the foams had cooled down, the thicknesses were likewise measured at three different places. The mean thickness and the initial thickness were needed to compute the expansion. (Example: (foam thickness−initial thickness)/initial thickness*100%=expansion).

The results are shown in the following table (11):

TABLE 11

Expansion of polymer foams/foam foils produced from thermally expandable plastisols (as per Example F1) at different oven residence times in Mathis Labcoater (at 200° C.).

| plastisol recipe (as per Example F1) | 1** | 7* |
|---|---|---|
| expansion after 60 s [%] | 3 | 4 |
| expansion after 90 s [%] | 353 | 380 |
| expansion after 120 s [%] | 495 | 515 |
| expansion after 150 s [%] | 511 | 522 |

**= comparative example
*= inventive example

Compared with the current standard plasticizer DINP, significantly higher foam heights/expansion rates are achieved after a residence time of 90, 120 and 150 seconds. The completeness of the decomposition of the blowing agent used and hence the progress of the expansion process is also evident from the colour of the foam produced. The less the yellowness of the foam, the further the progress of the expansion process.

2. Determination of Yellowness Index

The YD 1925 yellowness index is a measure of yellow discolouration of a sample specimen. This yellowness index is of interest in the assessment of foam foils in two respects. First, it indicates the degree of decomposition of the blowing agent azodicarbonamide (=yellow in the undecomposed state) and, secondly, it is a measure of thermal stability (discolourations due to thermal stress). Colour measurement of the foam foils was done using a Spectro Guide from Byk-Gardner. A (commercially available) white reference tile was used as background for the colour measurements. The following settings were used for the parameters:
 illuminant: C/2°
 number of measurements: 3
 display: CIE L*a*b*
 index measured: YD1925

The measurements themselves were carried out at 3 different places on the samples (at a plastisol blade thickness of 200 μm for effect and flat foams). The values obtained from the 3 measurements were averaged.

The yellowness index determined for the polymer foams/foam foils obtained in Example F2 is shown in the following Table (12).

TABLE 12

$Y_i$ D1925 yellowness indices of polymer foams obtained in Example F1.

| plastisol recipe (as per Ex. F1) | 1** | 7* |
|---|---|---|
| yellowness index after 60 s [%] | 69 | 70 |
| yellowness index after 90 s [%] | 34 | 36 |
| yellowness index after 120 s [%] | 25 | 24 |
| yellowness index after 150 s [%] | 25 | 24 |

**= comparative example
*= inventive example

The yellowness indices of the foams are close together throughout the entire residence-time span. After 120 and 150 seconds, the yellowness index is even at a lower level. The expansion rates and the yellowness indices demonstrate that fast processing is possible with the plastisols of the present invention.

In addition to the presented example, foams containing fillers and/or pigments and also effect or flat foams are also for example obtainable with the esters of the present invention. Effect foams refers to foams having a special texture on the surface. These foams are frequently also referred to as "bouclé" foams after the appearance pattern known from the textile sector.

Useful fillers include, for example, calcium carbonates, silicates, talc, kaolin, mica, feldspar, wollastonite, sulphates, carbon black and microspheres. Fillers are frequently used at not more than 150 parts by mass, preferably at not more than 100 parts by mass, per 100 parts by mass of polymer.

The invention claimed is:

1. An ester mixture, comprising a compound of formula (I):

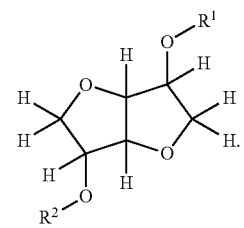

wherein:
 $R^1$ and $R^2$ independently represent a C8-acyl group or a C10-acyl group, in which
  the C8-acyl group is derived from a C8-alkyl linear carboxylic acid, a C8-alkyl branched carboxylic acid, or a C8-alkene carboxylic acid that may be partially or completely epoxidized, and
  the C10-acyl group is derived from a C10-alkyl linear carboxylic acid, a C10-alkyl branched carboxylic acid, or a C10-alkene carboxylic acid that may be partially or completely epoxidized; and
 a proportion of C8-acyl groups relative to a total sum of the C8-acyl groups and C10-acyl groups in the ester mixture is from 50 mol % to 85 mol %.

2. The ester mixture according to claim 1, wherein the proportion of the C8-acyl groups relative to the total sum of the C8-acyl groups and the C10-acyl groups in the ester mixture is from 50 mol % to 75 mol %.

3. The ester mixture according claim 1, wherein the proportion of the C8-acyl groups relative to the total sum of the C8-acyl groups and the C10-acyl groups in the ester mixture is from 50 mol % to 65 mol %.

4. The ester mixture according to claim 1, wherein a sum of the C8-acyl groups and the C10-acyl groups in the ester mixture has a proportion above 50 mol % relative to all acid chains in the ester mixture.

5. The ester mixture according to claim 1, wherein $R^1$ is selected from the group consisting of
 a C8-acyl group derived from a C8-alkyl linear carboxylic acid, and
 a C10-acyl group derived from a C10-alkyl linear carboxylic acid.

6. The ester mixture according to claim 1, wherein $R^2$ is selected from the group consisting of
 a C8-acyl group derived from a C8-alkyl linear carboxylic acid, and
 a C10-acyl group derived from a C10-alkyl linear carboxylic acid.

7. The ester mixture according claim 1, comprising a mixture of the following three compounds:

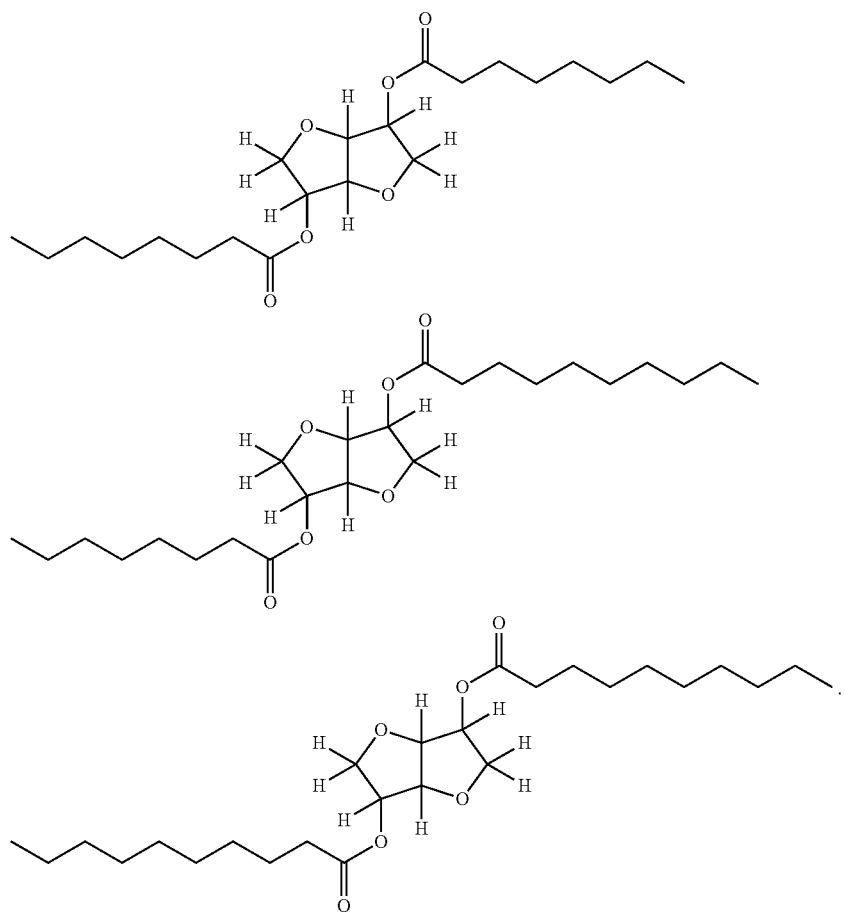

8. A composition, comprising:
 the ester mixture of claim 1; and
 a high boiler, a low boiler, or a mixture thereof.

9. The composition according to claim 8, wherein a proportion of high boilers is less than 15 area % based on ester signals in a gas-chromatographic analysis of the composition.

10. The composition according to claim 8, wherein a proportion of low boilers is less than 4.5 area % based on the ester signals in a gas-chromatographic analysis of the composition.

11. A polymer composition, comprising:
 the ester mixture of claim 1; and
 a polymer.

12. A method of plasticizing a polymer, the method comprising combining the ester mixture of claim 1 with a polymer.

13. A method for producing an ester mixture of claim 1, comprising:
 a) admixing n-octanoic acid and n-decanoic acid with a dianhydrohexitol;
 b) esterifying the n-octanoic acid and the n-decanoic acid with the dianhydrohexitol in the presence of a catalyst; and
 c) terminating the esterifying b) when a proportion of monoester of the dianhydrohexitol is below 2.0 area % based on a gas-chromatographic analysis.

14. The method according to claim 13, wherein the catalyst is hypophosphorous acid.

15. The method according to claim 13, wherein the n-octanoic acid and the n-decanoic acid are admixed in a molar ratio from 85:15 and 45:55.

16. The method according to claim 13, wherein the n-octanoic acid and the n-decanoic acid are admixed in a molar ratio from 80:20 and 45:55.

17. The ester mixture according to claim 1, wherein at least one $R^1$ or $R^2$ group contained in a compound of formula (I) in the ester mixture is defined as a C8-alkene carboxylic acid that is partially or completely epoxidized or as a C10-alkene carboxylic acid that is partially or completely epoxidized.

* * * * *